United States Patent [19]
Cueman et al.

[11] Patent Number: 5,014,691
[45] Date of Patent: May 14, 1991

[54] ANKLE BRACE WITH DENSIFIED BATTING

[75] Inventors: Glenn F. Cueman; Henry L. Richbourg, Jr., both of Charlotte; Barnwell S. Ramsey, Statesville, all of N.C.

[73] Assignee: Clintex Corporation, Huntersville, N.C.

[21] Appl. No.: 465,811

[22] Filed: Jan. 16, 1990

[51] Int. Cl.$^5$ .............................................. A61F 5/00
[52] U.S. Cl. ............................. 128/80 H; 128/80 R; 128/87 R; 128/90; 128/156
[58] Field of Search .................. 128/80 R, 80 A, 80 B, 128/80 E, 80 H, 89 R, 90, 156; 2/22, 23, 24

[56] References Cited

U.S. PATENT DOCUMENTS

| | | | |
|---|---|---|---|
| 3,298,365 | 1/1967 | Lewis | 128/80 R |
| 4,638,794 | 1/1987 | Grisar | 128/80 H |
| 4,651,726 | 3/1987 | Holland | 128/80 H |
| 4,865,023 | 9/1989 | Craythorne et al. | 128/80 H |
| 4,893,617 | 1/1990 | Bartial et al. | 128/90 |

Primary Examiner—Richard J. Apley
Assistant Examiner—Lynne Reichard
Attorney, Agent, or Firm—Ralph H. Dougherty

[57] ABSTRACT

A brace for an ankle includes first and second ankle guards for placement over the medial and lateral portions of the ankle, respectively. A foot sole piece connects the two ankle guards. A first densified batting pad attaches to the first ankle guard so that the pad makes contact with the medial portion of the ankle. A second densified batting pad is similarly attached to the second ankle guard so that it makes contact with the lateral portion of the ankle. The brace also includes means for securing the brace to the ankle, such as VELCRO closures.

11 Claims, 3 Drawing Sheets

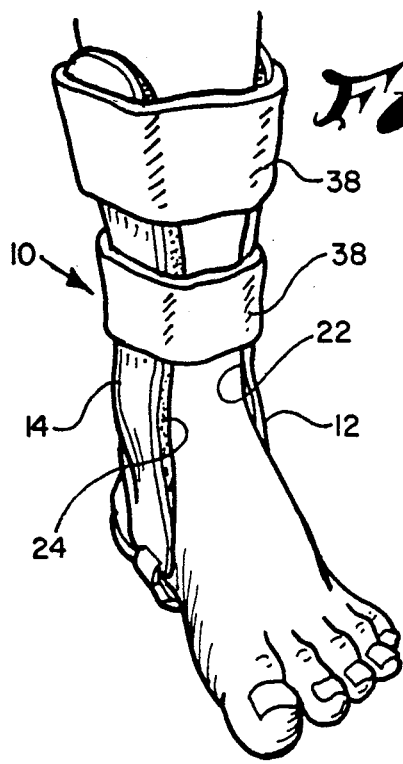
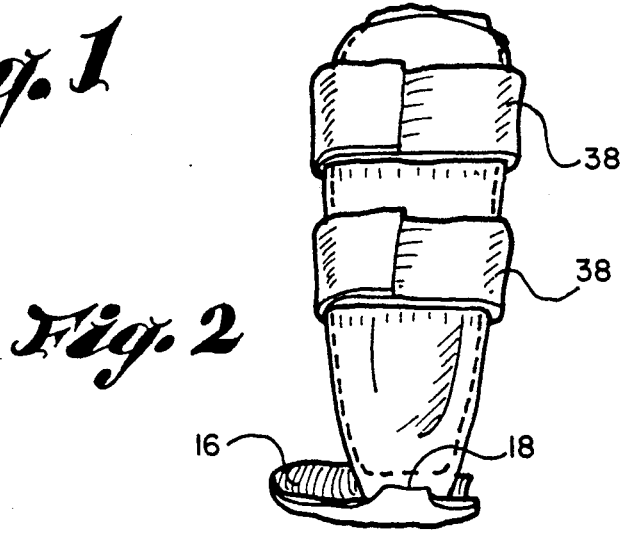
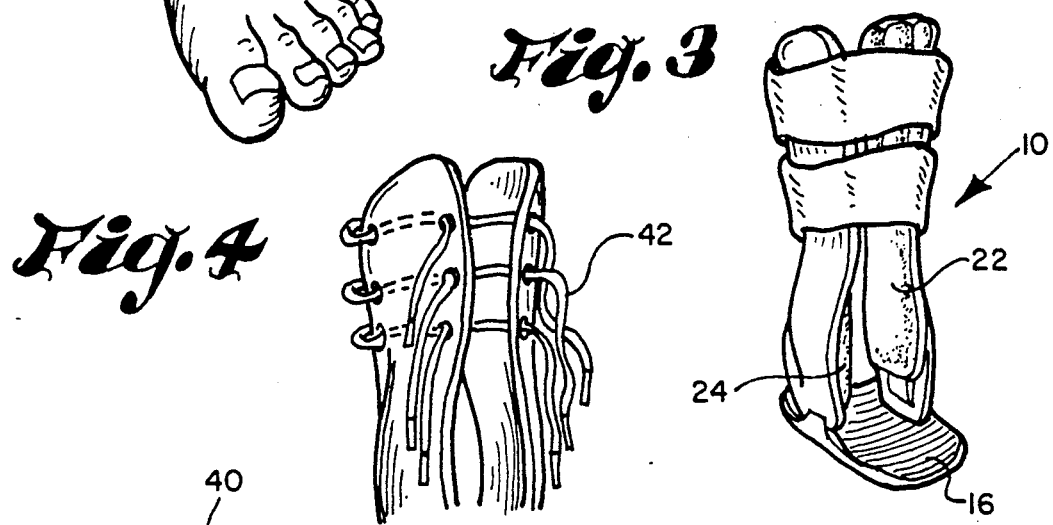
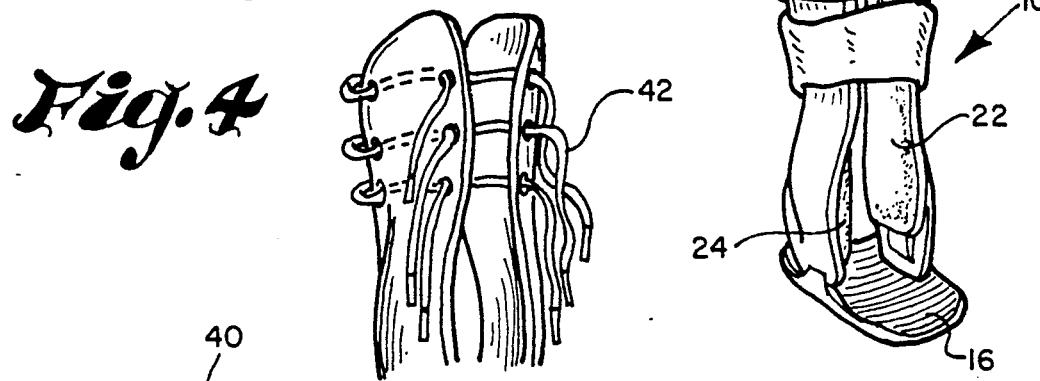
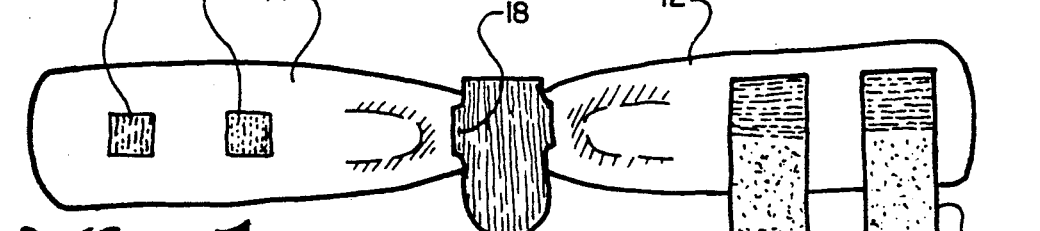
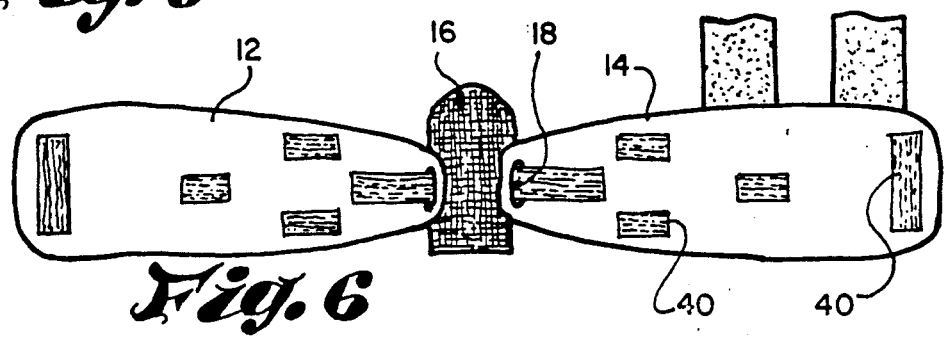

ANKLE BRACE WITH DENSIFIED BATTING

BACKGROUND OF THE INVENTION

1. Field of the Invention

The present invention generally relates to braces and, more particularly, is concerned with ankle braces with densified batting.

2. Description of the Prior Art

After an ankle injury, the joint needs to be stabilized to prevent further injury and to allow healing to occur. In the case of severe injury, such as a fracture, a plaster cast must be applied, completely immobilizing the foot, ankle, and lower leg. As the fracture heals, less restrictive forms of bracing are used, allowing ambulation. In less severe injuries, such as sprains, various types of braces and splints can be utilized. A key objective is to limit movement enough to allow healing, while permitting as much comfort and mobility as possible. Active use of the injured extremity promotes healing through better circulation and rehabilitation of muscle tissue.

The ankle can be a difficult joint to immobilize, since motion occurs in two planes—dorsiflexion/plantarflexion and inversion/eversion. Some rigid, lace-up braces immobilize in both planes, severely restricting normal gait. These are also most uncomfortable, allowing little beneficial motion. Other braces use ankle guards lined with air or gel filled compartments, and secured with VELCRO closures. These braces help stabilize the joint medially and laterally, but allow dorsiflexion/plantarflexion. This permits healing to occur while allowing reasonably normal gait. Unfortunately, these air or gel filled liners must utilize a vinyl, or similar, impervious material in their construction to contain the air or gel. This renders the brace very hot and uncomfortable, due to the inability of this material to absorb or wick away moisture. These liners can also leak, creating instability and potential re-injury. Some urethane foam liners have been developed which partially solve the comfort and leakage problem, but do not provide "fluid compression" or massage as the air and gel products do, eliminating necessary support and healing characteristics of the air and gel products. Since the bony structure of the ankle moves constantly within the brace, it required "fluid" support, maintaining stability while providing comfort.

The applicants are aware of the following U.S. Patents concerning ankle brace related inventions.

| U.S. Pat. No. | Issue Date | Inventor | Title |
| --- | --- | --- | --- |
| 3,955,565 | 05/11/76 | Johnson | ORTHOPEDIC APPARATUS |
| 4,280,489 | 07/28/81 | Johnson | ANKLE BRACE |
| 4,287,920 | 09/08/81 | Johnson | SELF-SEALING VALVE |
| 4,628,945 | 12/16/86 | Johnson | INFLATABLE ANKLE BRACE WITH POROUS COMPRESSIBLE FILLER |

U.S. Pat. No. 3,955,565 relates to an orthopedic apparatus utilizing the stirrup design and a series of air bags or similar means capable of assuming a normally flattened configuration but which when inflated with air through a valved inlet port are capable of being radially expanded to conform to the irregular shape of the limb or other body part with which such air bag is intended to engage.

The ankle brace taught in U.S. Pat. No. 4,280,489 teaches an ankle brace using an inflatable bladder as a flexible support member for stabilizing the ankle against inversion and eversion without limiting normal plantarflexion and dorsiflexion of the ankle.

U.S. Pat. No. 4,287,920 teaches a self-sealing valve invention for which a fluid-filled or inflatable article, such as an air bag.

The inflatable ankle brace with porous compressible filler in U.S. Pat. No. 4,628,945 appears to be an improvement to U.S. Pat. No. 3,955,565, whereby a resilient, compressible filler member, porous and permeable to air, is disposed interiorly of each airbag to serve the dual function of pre-inflating the airbag and simultaneously providing a cushioning member.

Applicants are unaware of any prior art that accomplishes the objects of the present invention. Consequently, a need exists for an ankle brace with densified batting.

SUMMARY OF THE INVENTION

The present invention is an innovative ankle brace with densified batting, which overcomes the problems and satisfies the needs previously considered.

The invention utilizes a stirrup design which provides support without restricting normal gait. In the preferred embodiment, plastic shells or guards are lined with a material known as densified batting, made from fibers, typically polyester, which are treated with lubricants, typically silicone, allowing the fibers to slide on one another. This sliding action provides a fluid-like feel, similar to gel or water, while being completely breathable. As used herein, the term "densified batting" means a group of fibers which have been compressed in a manner which alters the shape and/or compression characteristics of the fibers, and which have been treated with one or more lubricants. Typically, the fibers are polyester and the lubricant is silicone. Densification allows excellent control of density and shape, which is atypical when dealing with fibrous materials of this type. The densified bat is then enclosed in a fabric cover, providing a smooth, washable surface adjacent to the skin. The material can also be sewn or ultrasonically welded, which can enhance contouring and localized pressure points. Segments of the densified batting can also be combined with urethane foam, enhancing the non-fluid support of that material while providing a cost savings over using 100% densified batting. The densified batting pads are marketed under the trademark SHEARTEX TM.

In summary, the invention encompasses a brace for an ankle which includes first and second ankle guards for placement over the medial and lateral portions of the ankle, respectively. A foot sole piece connects the two ankle guards. A first densified batting pad attaches to the first ankle guard so that the pad makes contact with the medial portion of the ankle. A second densified batting pad is similarly attached to the second ankle guard so that it makes contact with the lateral portion of the ankle. The brace also includes a means for securing the brace to the ankle, such as VELCRO closures.

OBJECTS OF THE INVENTION

The principal object of the present invention is to provide brace means for limiting ankle movement sufficiently to allow healing of an injured ankle, while permitting as much comfort and mobility as possible.

Another object of the invention is to provide a safeguard mechanism against reinjury to the ankle.

Yet another object of the invention is to provide an ankle injury prevention mechanism for use by athletes or other active individuals.

BRIEF DESCRIPTION OF THE DRAWINGS

The foregoing and other objects will become more readily apparent by referring to the following detailed description and the appended drawings in which:

FIG. 1 is an isometric view of the invented brace in use on a human ankle.

FIG. 2 is a side isometric view of the invented brace shown in FIG. 1.

FIG. 3 is a generally rear isometric view of the embodiment of the invention shown in FIG. 2.

FIG. 4 is a partial isometric view of an alternative embodiment of the invention showing a lacing mechanism as the means for securing the brace to the ankle.

FIG. 5 is a plan view of the outstretched exterior of the invention shown in FIG. 1.

FIG. 6 is a plan view of the outstretched interior of the invention shown in FIG. 1.

DETAILED DESCRIPTION

Figure 7:
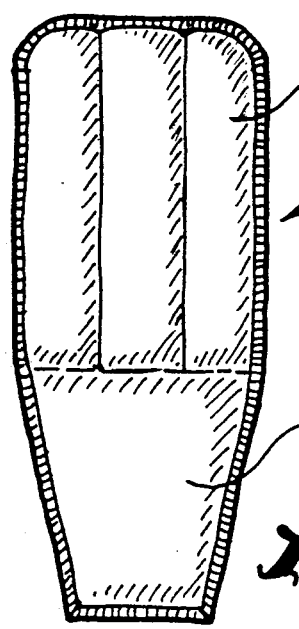
FIG. 7 is an isolated plan view of a densified batting pad shown in FIG. 1.

Referring now to the drawings, and more particularly, to FIG. 1, an ankle brace with densified batting, generally designated 10, comprises the preferred embodiment of the present invention.

The brace 10 for an ankle includes a first elongated ankle guard 12 for placement over the medial portion of the ankle, and a second elongated ankle guard 14 for placement over the lateral portion of the ankle. The opposed first and second ankle guards 12, 14 are made of material sufficiently rigid to inhibit inversion and eversion. In the preferred embodiment they are made of plastic and are convexly contoured so that they fit over the medial and lateral portions of the ankle, respectively. A foot sole piece 16 connects the first ankle guard 12 to the second ankle guard 14. The foot sole piece 16 is a thin heel-shaped pad having extensions that fit through apertures 18 in the first and second ankle guards 12, 14, and attach to VELCRO closures 40.

Figure 9:
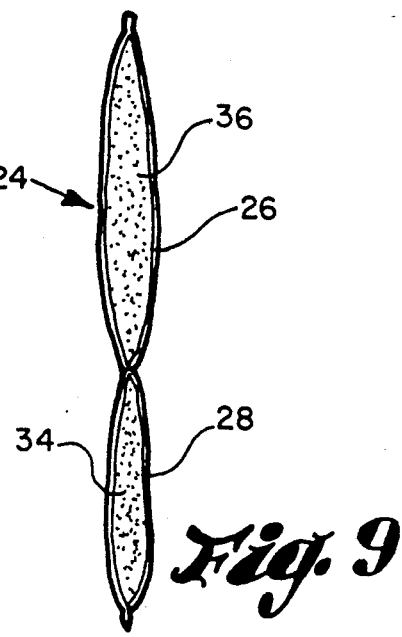
FIG. 9 is a vertical section of an alternative embodiment of the densified batting pad shown in FIG. 8, showing a segmented cushion-like pad, wherein a lower segment is completely filled with densified batting and an upper segment is completely filled with non-densified batting.
Figure 8:
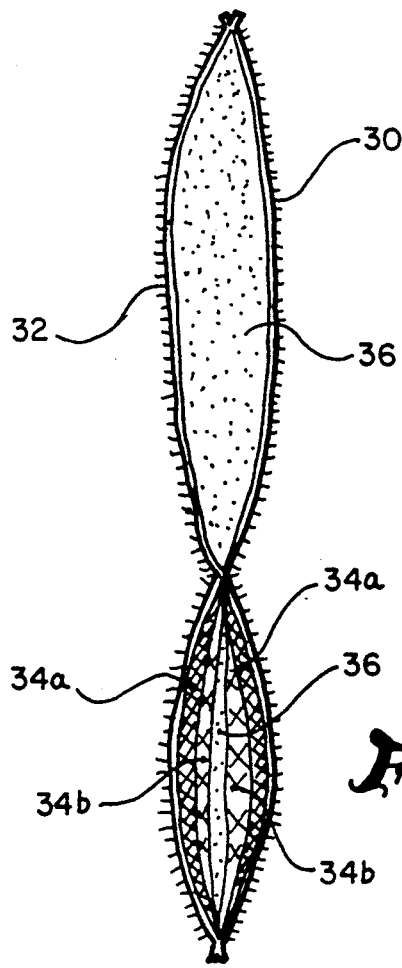
FIG. 8 is a vertical section of the densified batting pad shown in FIG. 7, showing the preferred embodiment.
Figure 10:
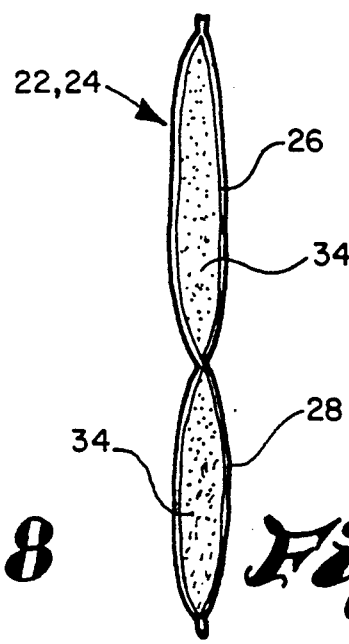
FIG. 10 is a vertical section of an alternative embodiment of the densified batting pad shown in FIG. 8, showing a segmented cushion-like pad, wherein both the upper and lower segments are completely filled with densified batting.

A first densified batting pad 22 attaches to the inside of the first ankle guard 12 so that the first densified batting pad 22 is in contact with the medial portion of the ankle. A second densified batting pad 24 attaches to the inside of the second ankle guard 14 so that the second densified batting pad 24 is in contact with the lateral portion of the ankle. Optionally, a single densified batting pad can be used to make contact with both the medial and the lateral portions of the ankle. In the preferred embodiment, shown in FIG. 8, each densified pad 22, 24 includes a non-densified batting pad portion 36, such as urethane foam, of sufficient length to cover the medial or lateral portion of a human ankle. Two layers of densified batting 34, a soft densified batting 34b surrounded by an outer layer of hard densified batting 34a, are placed on top of the non-densified batting pad 36. A first cover 30, preferably nylon, is placed on top of the densified and non-densified batting 34, 36. A second cover 32 is placed underneath the non-densified batting 36. The second cover is adapted for attachment to VELCRO closures 40. The first and second covers 32, 34 are then sewn together to encase the densified and non-densified batting 34, 36. The covers 32, 34 can be ultrasonically welded and/or sewn in a variety of configurations to enhance contouring and localized pressure points, and to segment the densified and non-densified batting 34, 36 into particular areas within the pad. Alternatively, as shown in FIG. 9, each densified batting pad 22, 24 is a segmented cushion-like pad, wherein an upper segment 26 is completely filled with non-densified batting 36, such as urethane foam, and a lower segment 28 is completely filled with densified batting 34. Another alternative is for each densified batting pad 22, 24 to have a cushion-like pad completely filled with densified batting 34, as shown in FIG. 10. In this case the pads 22, 24 need not be segmented. Pads 22, 24 can be sewn or ultrasonically welded and have washable exterior covers 30, 32, as shown in FIG. 9. Preferably, pads 22, 24 are made of a nylon exterior cover 30 which makes contact with the ankle, and a VELCRO exterior cover 32 which attaches to VELCRO closures 40 on the interior of ankle guards 12, 14.

Figure 11:
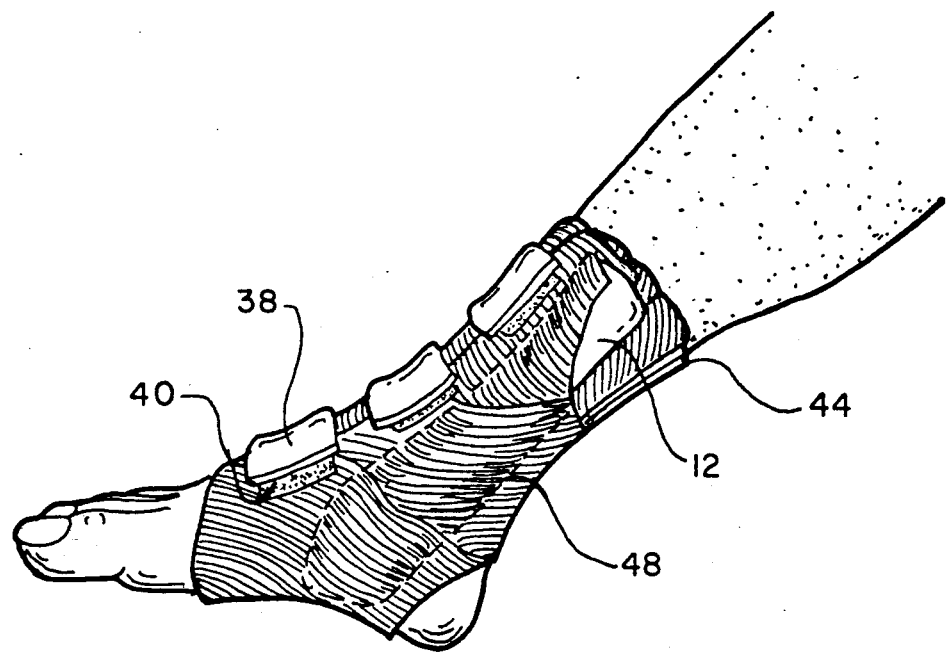
FIG. 11 is a partially cut away isometric view of an alternative embodiment of the ankle brace wherein means for securing the brace includes a cut-and-sew ankle support.

In the preferred embodiment, the means for securing the brace to the ankle is VELCRO 38 attached to VELCRO closures 40. Use of laces 42 to secure the brace to the ankle is an alternative embodiment (See FIG. 3). As shown in FIG. 11 which depicts another alternative embodiment for securing the brace 10 to the ankle, a standard cut-and-sew ankle brace 44, in conjunction with the first and second ankle guards 12, 14.

Figure 12:
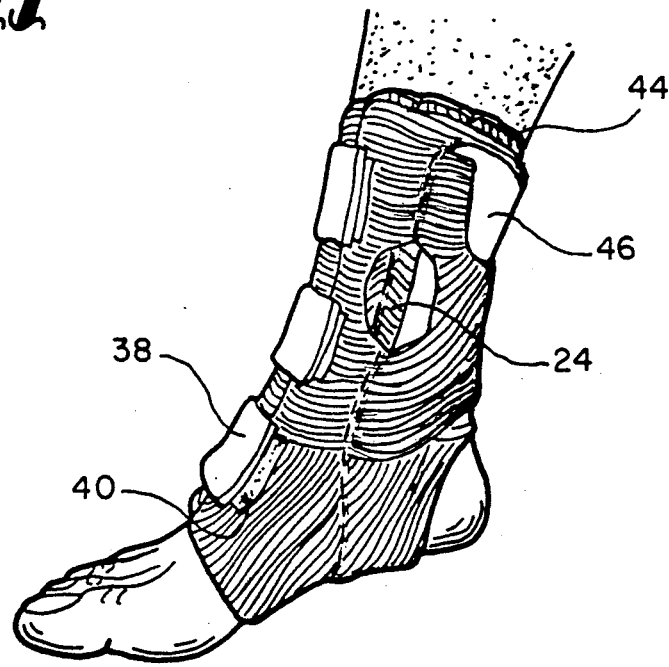
FIG. 12 is a partially cut away isometric view of another ankle brace embodiment having a single ankle guard that encompasses the lateral and posterier portions of the ankle.

Alternatively, as shown in FIG. 12, a single ankle guard 46 encompassing the ankle both posteriorly as well as laterally, can be used in conjunction with a standard cut-and-sew ankle brace 44. The ankle guard 44 or guards 12, 14 are contained in a stay pocket 48 sewn onto the cut-and-sew ankle brace 44, or, alternatively, may be attached by means such as VELCRO. Densified batting pads 22, 24 are attached inside the cut-and-sew ankle brace 44 to make contact with the medial and lateral portions of the ankle, respectively. As used herein, a "cut-and-sew brace" means a flexible means of support for a limb fashioned from material cut, sewn and adapted for placement over the limb.

SUMMARY OF THE ACHIEVEMENTS OF THE OBJECTS OF THE INVENTION

From the foregoing, it is readily apparent that we have invented an improved ankle brace with densified batting which achieves the objectives of providing limited ankle movement enough to allow healing, while permitting as much comfort and mobility as possible, providing a safeguard mechanism against reinjury to the ankle, and providing an ankle injury prevention mechanism for use by athletes or other active individuals.

It is to be understood that the foregoing description and specific embodiments are merely illustrative of the best mode of the invention and the principles thereof, and that various modifications and additions may be made to the device by those skilled in the art, without departing from the spirit and scope of this invention, which is therefore understood to be limited only by the scope of the appended claims.

We claim:

1. A brace for an ankle, said ankle having a medial portion and a lateral portion, comprising:
   (a) means for stabilizing said ankle medially and laterally, while permitting dorsiflexion and plantarflexion, said stabilizing means including:
      (i) a first ankle guard for placement over said medial portion of said ankle;
      (ii) a second ankle guard for placement over said lateral portion of said ankle; and
      (iii) a foot sole piece connecting said first ankle guard to said second ankle guard;
   (b) at least one densified batting pad attachable to said stabilizing means so that said densified batting pad is in contact with said medial and lateral portions of said ankle, wherein a first densified batting pad and a second densified batting pad is provided, said first densified batting pad being attached to said first ankle guard so that said first densified batting pad is in contact with said medial portion of said ankle, and said second densified batting pad being attached to said second ankle guard so that said second densified batting pad is in contact with said lateral portion of said ankle, wherein said first and second densified batting pads each comprise:
      (i) a non-densified batting pad of sufficient length to cover said medial or lateral portions of said ankle;
      (ii) two layers of densified batting, a soft densified batting surrounded by an outer layer of hard densified batting, positioned at one end of said non-densified batting pad;
      (iii) a first cover, covering both said densified and said non-densified batting;
      (iv) a second cover underneath said non-densified batting, adapted for attachment to hook and loop type closures; and
      (v) means for connecting said first cover and said second cover together to encase and segment said densified batting and said non-densified batting; and
   (c) means for securing said brace to said ankle.

2. The brace for an ankle as set forth in claim 1, wherein said stabilizing means includes an ankle guard for placement over said medial portion and said lateral portion of said ankle.

3. The brace for an ankle as set forth in claim 1, wherein said first and second ankle guards are selected from the group comprising plastic, vinyl, and rubber.

4. The brace for an ankle as set forth in claim 1, wherein said first and second ankle guards are convexly contoured so that said first and second ankle guards fit over said medial and lateral portions of said ankle, respectively.

5. The brace for an ankle as set forth in claim 1, wherein said foot sole piece comprises a thin heel-shaped pad, made from weaved material selected from the group comprising wool, hair, and cotton, said pad having extensions that fit through apertures in said first and second ankle guards and attached to hook and loop type closures.

6. The brace for an ankle as set forth in claim 1, wherein said first and second densified batting pads each comprise a segmented cushion-like pad, wherein an upper segment is completely filled with non-densified batting, and a lower segment is completely filled with densified batting.

7. The brace for an ankle as set forth in claim 1, wherein said first and second densified batting pads each comprise a cushion completely filled with densified batting.

8. The brace for an ankle as set forth in claim 1, wherein said means for securing said brace to said ankle comprises hook and loop type closures.

9. The brace for an ankle as set forth in claim 1, wherein said means for securing said brace to said ankle comprises laces.

10. The brace for an ankle as set forth in claim 1, wherein said means for securing said brace to said ankle comprises a standard cut-and-sew ankle brace having a stay pocket sewn onto said cut-and-sew ankle brace, a single ankle guard for encompassing said ankle both posteriorly as well as laterally, said said stay pocket adapted for and receiving said ankle guard, and said densified batting pads attached inside said cut-and-sew ankle brace so as to make contact with said medial and lateral portions of said ankle.

11. The brace for an ankle as set forth in claim 1, wherein said means for securing said brace to said ankle comprises a standard cut-and-sew ankle brace having a stay pocket sewn onto said cut-and-sew ankle brace, a first ankle guard and a second ankle guard for encompassing said ankle laterally, said said stay pocket adapted for and receiving said ankle guards, and said densified batting pads attached inside said cut-and-sew ankle brace so as to make contact with said medial and lateral portions of said ankle.

* * * * *

UNITED STATES PATENT AND TRADEMARK OFFICE
CERTIFICATE OF CORRECTION

PATENT NO. : 5,014,691
DATED : May 14, 1991
INVENTOR(S) : Glenn F. Cueman, Henry L. Richbourg, Jr., and Barnwell S. Ramsey It is certified that error appears in the above—identified patent and that said Letters Patent is hereby corrected as shown below:

On the title page:
In (73) Assignee: "Clintex" should read -- Clinitex --

Signed and Sealed this

Thirty-first Day of May, 1994

Attest:

BRUCE LEHMAN

Attesting Officer

Commissioner of Patents and Trademarks